(12) United States Patent
Podobnik et al.

(10) Patent No.: US 7,585,496 B2
(45) Date of Patent: Sep. 8, 2009

(54) STABLE PHARMACEUTICAL COMPOSITION GRANULOCYTE-COLONY STIMULATING FACTOR

(75) Inventors: Barbara Podobnik, Ljubljana (SI); Vladka Gaberc Porekar, Ljubljana (SI); Viktor Menart, Logatec (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 10/577,285

(22) PCT Filed: Nov. 4, 2003

(86) PCT No.: PCT/IB03/05575

§ 371 (c)(1), (2), (4) Date: Oct. 10, 2006

(87) PCT Pub. No.: WO2005/042024

PCT Pub. Date: May 12, 2005

(65) Prior Publication Data

US 2007/0081971 A1    Apr. 12, 2007

(51) Int. Cl.
*A61K 45/00* (2006.01)
*A61K 38/19* (2006.01)
*C07K 14/00* (2006.01)
*A61K 47/02* (2006.01)
*A61K 47/12* (2006.01)

(52) U.S. Cl. ............... 424/85.1; 530/351; 514/12
(58) Field of Classification Search ............... None
See application file for complete search history.

(56) References Cited

U.S. PATENT DOCUMENTS

| | | | | |
|---|---|---|---|---|
| 5,284,656 | A * | 2/1994 | Platz et al. | 424/435 |
| 5,919,757 | A | 7/1999 | Michaelis et al. | |
| 6,432,449 | B1 * | 8/2002 | Goldenberg et al. | 424/486 |
| 6,579,521 | B2 * | 6/2003 | Sahner | 424/85.2 |
| 6,776,983 | B1 * | 8/2004 | Sumida et al. | 424/85.1 |
| 6,875,432 | B2 * | 4/2005 | Liu et al. | 424/130.1 |

FOREIGN PATENT DOCUMENTS

| | | |
|---|---|---|
| EP | 1 129 720 | 9/2001 |
| EP | 0 988 861 | 3/2002 |

* cited by examiner

*Primary Examiner*—Lorraine Spector
*Assistant Examiner*—Elly-Gerald Stoica
(74) *Attorney, Agent, or Firm*—Luedeka, Neely & Graham, P.C.

(57) ABSTRACT

The present invention provides a new stable pharmaceutical composition of granulocyte-colony stimulating factor (G-CSF).

19 Claims, 5 Drawing Sheets

STABLE PHARMACEUTICAL COMPOSITION GRANULOCYTE-COLONY STIMULATING FACTOR

FIELD OF THE INVENTION

The present invention relates to a stable pharmaceutical composition which comprises granulocyte-colony stimulating factor (G-CSF).

BACKGROUND OF THE INVENTION

Human G-CSF belongs to hematopoetic growth factors which have a decisive role in the formation of neutrophils. G-CSF is used in medicine in the field of hematology and oncology. Today, two forms of G-CSF for clinical use are in the market: lenograstim which is glycosylated and is produced in mammalian cells, specifically a CHO cell line (Holloway C J (1994) *Eur J Cancer* 30A Suppl 3:S2-S6; EP 169566), and filgrastim which is non-glycosylated and is produced in a bacterium *E. coli* (EP 237545).

It is known from the literature that especially non-glycosylated forms of G-CSF are particularly unstable in vitro compared to glycosylated form of G-CSF which, is obtained from CHO cells (Oh-eda et al (1990) *J Biol Chem* 265(20): 11432-35). Due to different stabilities of glycosylated and non-glycosylated G-CSF the prior art approaches for preparation of stable pharmaceutically acceptable G-CSF differ according to the presence/absence of glycosylation. Especially in the case of non-glycosylated G-CSF which is a hydrophobic protein a preparation of stable pharmaceutically acceptable compositions that would support stability of the pharmaceutical proteins on longer storage periods and upon medical application is a difficult task, represents a special challenge and requires specially selected measures.

Stabilized compositions of non-glycosylated G-CSF are described in EP 373679 and are characterized essentially by advantageously providing G-CSF stability at low conductivity and at an acidic pH value ranging from 2.75 to 4.0. However, various sugars or sugar alcohols, amino acids, polymers and detergents can be added for better G-CSF stability. In particular, it is stressed that pH of the composition should be less than 4 in order to reduce aggregate formation and to increase the G-CSF stability. The aggregate formation and the reduced stability of pharmaceutical compositions comprising G-CSF at pH above 4.0 described in EP 373679 are in accordance with the results obtained from prior art literature (Kuzniar et al (2001) *Pharm Dev Technol* 6(3):441-7; Bartkowski et al (2002) *J Protein Chem* 21(3):137-43; Narhi et al (1991) *J Protein Chem* 10(4): 359-367; Wang W (1999) *Int J Pharmaceut* 185:129-188.

Different approaches of stabilizing G-CSF are described in other patent and scientific literature. EP 1129720 discloses a stable aqueous composition of non-glycosylated bovine G-CSF that has pH in the range from 5 to 8 and comprises a salt comprising sulfate ions at the concentrations of from about 0.01 M to about 1.0 M.

In EP 607156 a pharmaceutical composition containing G-CSF for infusion and injection purposes is disclosed. The stabilisation of G-CSF is achieved by setting an acidic pH value which is favourable for G-CSF and by adding a mixture of various preservatives, different amino acids and a surfactant as stabilizers. It is not clear from the description whether glycosylated or non-glycosylated form of G-CSF was used. EP 674525 discloses aqueous pharmaceutical compositions of G-CSF stabilized in a buffer selected from the group consisting of a salt of citrate, maleate, a combination of phosphate and citrate, and arginine. In addition, at least one surfactant is added for achieving the G-CSF stability. It is not specified in the description whether either glycosylated or non-glycosylated form of G-CSF was used.

GB 2 193621 discloses a composition of glycosylated G-CSF with pH in the range from 7 to 7.5 which comprises at least one substance selected from the group consisting of a pharmaceutically acceptable surfactant, saccharide, protein and a high-molecular weight compound. Suitable high-molecular weight compounds include hydroxypropyl cellulose, hydroxymethyl cellulose, sodium carboxymethyl cellulose, polyethylene glycol, polyvinyl alcohol, and polyvinylpyrrolidone. In particular, compositions are stated to be advantageous which contain a surfactant.

In EP 1060746 a pharmaceutical composition comprising glycosylated G-CSF having pH about 6.5 is described in the presence of at least one pharmaceutically acceptable surfactant. The specification discloses the measurement of stability of desialylated G-CSF depending on pH. The results show a very low stability of desialyated G-CSF at pH in the range from about 5.0 to about 7.0.

EP 0988861 discloses a pharmaceutical composition of G-CSF, especially bovine G-CSF, where the G-CSF stability was achieved by addition of a stabilizing buffer, such as HEPES, TRIS, or TRICINE at the concentrations of about 1 M.

The lyophilised pharmaceutical compositions of G-CSF stabilized by the addition of maltose, cellobiose, gentiobiose, isomaltose, raffinose, trehalose or amino sugar are described in EP 0674524.

Glycosylated G-CSF compositions containing one or more amino acids at pH about 6.5 are described in EP 1197221, EP 1260230 and in EP 1329224, whereas the lyophilised compositions stabilized with amino-acids are described in EP 0975335. The method for prolonging the duration of pharmacological effect of G-CSF characterized in that a surfactant is present in a G-CSF water-soluble solution is described in JP2002371009.

Oral dosage form of G-CSF described in EP 0459795 is based on the stabilization with surfactants, fatty acids and enteric material. The compositions stabilized over long time with the addition of methionine are described in WO51629.

Although low ionic strength is preferential for pharmaceutical compositions of G-CSF, almost in every case in the patent and scientific literature various surfactants are added, either non-ionic, anionic or natural surfactants for prevention of G-CSF aggregation and denaturation at packing material surfaces. However, the surfactants in the G-CSF composition should preferably be avoided from a medical point of view since they can cause local irritations, they may contain toxic impurities which have to be controlled very carefully and additionally it is not always clear how they are metabolized and excreted. In addition, certain surfactants susceptible to autooxydation can damage proteins.

The object of the present invention is to provide a stable liquid pharmaceutical composition of non-glycosylated G-CSF which may enable a proper use of G-CSF as a pharmaceutical agent without the addition of surfactants and additives derived from human and/or animal origin. In particular, the pharmaceutical composition of the present invention has a long shelf life, is physiologically well-tolerated, simple to use and it is possible to dose it precisely.

SUMMARY OF THE INVENTION

The object of the invention is to provide a pharmaceutical composition of non-glycosylated G-CSF which is capable of beneficially stabilizing G-CSF.

The present invention provides a new stable pharmaceutical composition of G-CSF in accordance with claim 1. Preferred embodiments are set forth in the sub-claims. The present invention also provides a process according to claim 17, and a uses according to claims 18 and 19.

The pharmaceutical composition of the present invention is preferably formulated at pH above 4.0. The stabilization of G-CSF is achieved in the presence of an acid while the composition of the invention is preferably free of surfactants and free of additives derived from human and/or animal origin other than G-CSF (e.g. serum proteins). The pharmaceutical composition optionally further comprises a polyol and/or a pH buffering system and/or one or more pharmaceutically acceptable excipients. The pharmaceutical composition of the present invention is suitable for use in human and veterinary medicine and is pharmaceutically acceptable in a suitable administration form, especially for parenteral application, e.g. intramuscular, subcutaneous and/or intravenous application. In a particularly preferred embodiment, the pharmaceutical composition of the present invention is in a liquid, more preferably in an aqueous form.

DESCRIPTION OF THE INVENTION AND OF PREFERRED EMBODIMENTS

Figure 1:
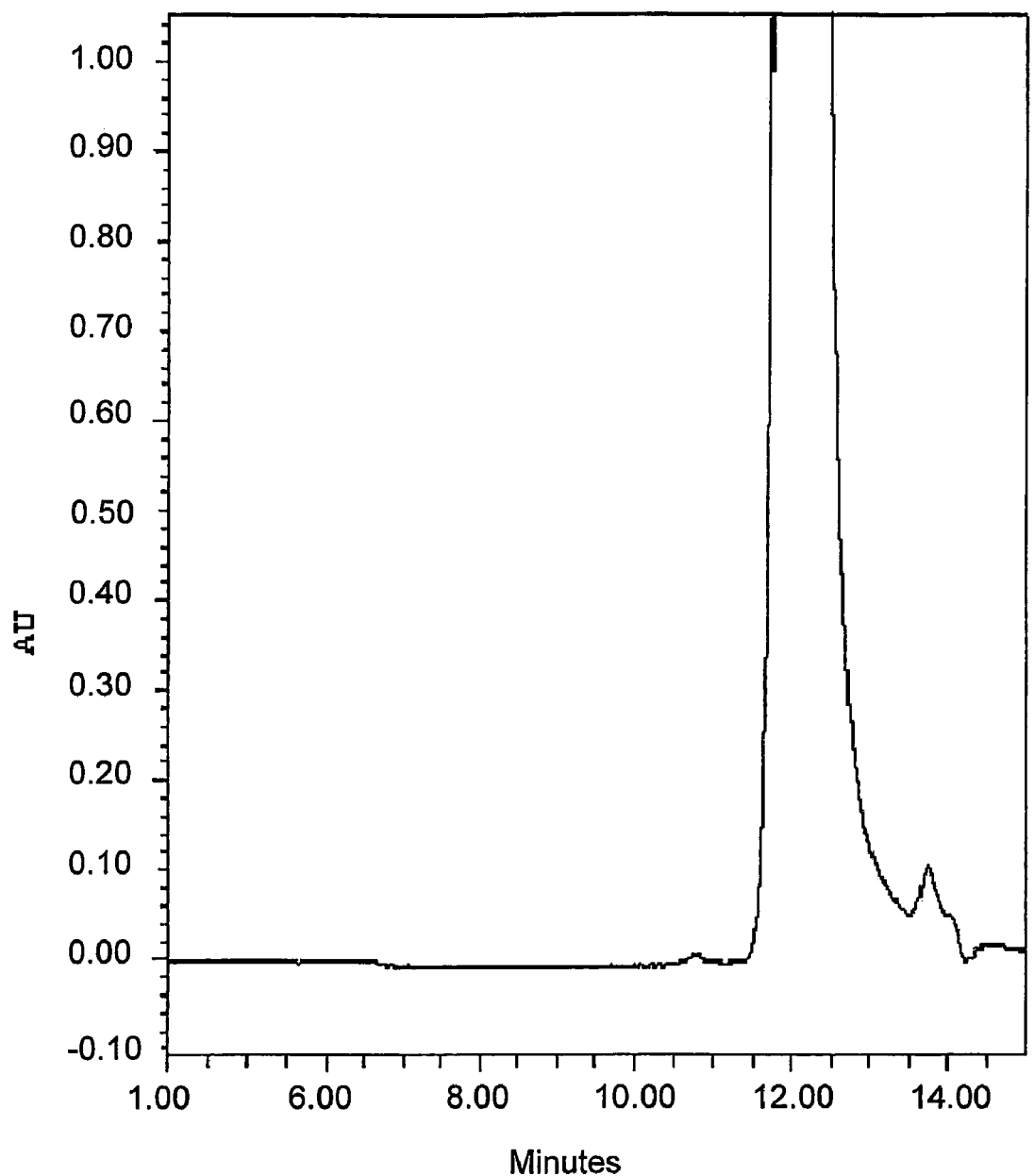
FIG. 1 shows SE-HPLC analysis of inventive sample comprising G-CSF after having been stored at 4° C. for 3 months.

It was surprisingly found that non-glycosylated G-CSF could be beneficially stabilized in a pharmaceutical composition which is free of surfactants and is preferably at pH above 4.0.

The present invention provides the pharmaceutical composition of G-CSF comprising:
(a) a therapeutically effective amount of G-CSF and
(b) an acid and
is preferably free of surfactants.

The composition of the invention is preferably prepared at pH above 4.0.

The present invention also provides the pharmaceutical composition of G-CSF which optionally further comprises in addition to components (a)-(b)
(c) a polyol and/or
(d) a pH buffering system and/or
(e) one or more pharmaceutically acceptable excipients.

The term 'granulocyte-colony stimulating factor (G-CSF) as used herein, refers to G-CSF which is capable of promoting the differentiation and proliferation of haematopoietic precursor cells and the activation of mature cells of the haematopoietic system and is selected from the group comprising the human G-CSF and derivatives and analogues which are defined below. Preferably, G-CSF relates to recombinant human G-CSF which is obtained by expression in *E. coli*.

The term 'therapeutically effective amount of G-CSF' as used herein, refers to the amount of G-CSF which enables the therapeutical effect of G-CSF.

The term 'polyol' as used herein, refers to any polyhydric alcohol, i.e., an alcohol containing two or more hydroxyl groups per molecule.

The term 'surfactant' as used herein, refers to colloidal aggregate of amphipathic (surfactant) molecules, which occurs at a certain concentration known as the critical micelle concentration. The typical number of aggregated molecules in a micelle (aggregation number) is 50 to 100.

The term 'free of surfactants' as used herein, refers to the condition that surfactants are either not present in the composition or are present in the amount below the detection limit.

The term 'G-CSF stabilizer' as used herein, refers to a pharmaceutical acceptable excipient, which has a stabilizing effect on G-CSF.

The term 'G-CSF stability' as used herein, refers to the maintenance of G-CSF content and to the maintenance of G-CSF biological activity. The G-CSF stability may be influenced inter alia by the following processes: adsorption of G-CSF to the container walls, denaturation or degradation of G-CSF and aggregate formation of e.g. G-CSF dimers and/or G-CSF multimers and/or similar molecules with higher molecular weight. These processes occur due to exposing of the samples to different conditions, e.g. highertemperature, inappropriate containers, use of wrong G-CSF stabilizers, sunshine, inappropriate way of storing, thawing/freezing and/or inappropriate isolation procedure.

The term 'free of additives derived from human and/or animal origin' as used herein, refers to the condition that additives which originate from human and/or animal and which are different from G-CSF, such as gelatin or serum proteins like human serum albumin or bovine serum albumin, are not intentionally added to the composition.

It has been surprisingly found that formulating G-CSF in the pharmaceutical composition of the present invention improves its stability at temperatures above refrigerator temperature (e.g. 2-8° C.), and also at room temperature (i.e. below 25° C.) and even higher temperatures (e.g. about 40° C.). This means that the composition can be stored at temperatures above refrigerator for a prolonged time and/or at higher temperatures for a certain period of time, without loosing significant amounts of activity and without significant degradation.

In the pharmaceutical compositions described in the prior art literature the non-glycosylated G-CSF was preferentially stabilized at pH below 4.0 either at low conductivity and at low acidic value or in the presence of different stabilizers. On the other hand all of the prior art G-CSF compositions stabilized at pH value of above 4.0 comprised different stabilizers among them surfactants being the most preferred. Additionally, it is often not clear from the prior art literature whether the glycosylated or non-glycosylated G-CSF was used in the G-CSF stability studies. The prior art studies of G-CSF stability at pH value of above 4.0 performed at low conductivity, and without the addition of a surfactant resulted in aggregate formation. Other approaches of stabilizing G-CSF at pH value of above 4.0 in the prior art literature comprise the addition of surfactant or various other excipients.

In spite of the approaches and the results described in the prior art literature it was surprisingly shown in the present invention that G-CSF stability could be achieved even at pH value of above 4.0 without the addition of a surfactant. Additionally, the G-CSF stability of the present invention could be achieved with an acid as a sole excipient to provide the environment suitable to beneficially stabilizing of G-CSF. Although not being limited in this way, no further G-CSF stabilizers e.g. pharmaceutically acceptable excipients may therefore be necessary for stabilizing G-CSF of the present invention. This is advantageously since the pharmaceutically acceptable excipients in pharmaceutical compositions have to be strictly controlled to avoid the toxic impurities. The impurities need to be removed in order to avoid administration of hardly controlled substances in human or animal body. On the other hand it is not clear how the pharmaceutically acceptable excipients are metabolized and excreted in the body what also needs to be taken in account in order to avoid side effects.

In some pharmaceutical compositions known from the prior art the surfactants like non-ionic detergents e.g. polysorbates are used. The use of auto-oxidation-prone surfactants in the G-CSF compositions may be regarded as problematic and preferably they should be avoided since they can cause the formation of OH radicals which may damage the proteins. The additions of surfactants may also cause local irritations at the administration site. Surfactants can also interfere with the determination of impurities, e.g. aggregates determined by SEC (analytical) methods. Therefore it is advantageously to keep the pharmaceutical compositions of G-CSF free of surfactants, as simple as possible, avoiding the use of additional excipients and keep pH of the composition suitable for administration to the patient.

The G-CSF composition of the present invention which is preferably free of surfactants is also better from the economical viewpoint. The composition is more easily performed, the expenses are lower, the composition is less time consuming and the patient receives lees additives in the organism. The pH value of above 4.0 is also better than pH value of below 4 since the subcutaneous administration can lead to local intolerances in patients due to too low pH values used.

Although not being restricted in this way, the pharmaceutical composition of the present invention may therefore preferably consist only of the aforementioned constituents a.-b., or optionally a.-c., a.-c. plus e, a.-d., a.-d. plus e., a.-b. plus e. or a.-b. plus d.-e.

The pharmaceutical composition of the present invention is preferably a liquid and particularly an aqueous pharmaceutical composition which maintains the G-CSF activity in long term storage. Such a liquid composition can be directly used for parenteral application such as subcutaneous, intravenous or intramuscular application without reconstitution, diluting or additional preparation steps which could lead to lowering or even a loss of G-CSF biological activity, and also can contribute to avoid additional technical problems occurring at the time of application. The use of a liquid pharmaceutical composition is therefore more practical as the use of lyophilized compositions. Liquid and particularly aqueous compositions of G-CSF are generally preferred over lyophilized compositions for preparing the clinical composition of G-CSF, because the reconstitution process of lyophilized compositions is time consuming, poses risks of improper handling of the protein composition, or may be reconstituted improperly, and certain additives such as stabilizers are usually required to retain sufficient activity of the drug.

Preferably, the pharmaceutical compositions of the present invention are substantially free of additives derived from human and/or animal origin such as serum albumin or purified gelatin as G-CSF stabilizers.

The G-CSF used in the pharmaceutical compositions of the present invention may be any non-glycosylated high-purity human G-CSF. Specifically, it may be derived from natural sources or genetically engineered so far as it has substantially the same biological activity as that of mammalian, particularly human G-CSF. Genetically engineered G-CSF may have the same amino acid sequence as that of native G-CSF or its analogues that may contain deletion, substitution or addition of one or more amino acids; G-CSF chemically modified with PEG or the like showing the same or improved biological activity are also included. The G-CSF used in the pharmaceutical compositions of the present invention may be prepared by any process, e.g. it may be extracted, isolated and purified by various techniques from cultures of bacterial cells such as *E. coli* and intracellularly in genetically modified yeasts or other appropriate organisms.

G-CSF used in the pharmaceutical composition of the present invention is most preferably produced by expression in *E. coli* and is preferably non-glycosylated.

The pharmaceutical composition of the present invention may comprise a therapeutically amount of G-CSF. Although the current therapeutical amounts of G-CSF on the market are from 0.3 to 0.96 mg/ml this may not be limiting for the G-CSF composition of the present invention.

The pH value of the G-CSF composition of the present invention is above 4.0, with a range from about 4.0 to about 5.0 being preferred, from about 4.2 to about 4.8 being more preferred and pH value of at about 4.4 being most preferred The preferred pH value range is preferably achieved by the use of acetic acid. Other suitable acids to obtain and maintain the desired pH value of above 4.0 include, but are not limited to HCl, methansulphonic acid, maleic acid, citric acid, glutamic acid, malonic acid, lactic acid, sulphuric acid, phosphoric acid and other pharmaceutically acceptable acids or their mixtures. The concentration of the acid in the composition depends on the desired pH value of the composition.

In another embodiment the desired pH value may be obtained by using different acids selected from the group comprising acetic acid citric acid, phosphoric acid and other suitable acids whereby the fine tuning of the final pH value is achieved by the addition of a pH adjusting agent selected from a group comprising NaOH, TRIS or any other suitable base. By the addition of the above mentioned acid and base a suitable pH buffering system e.g. acetic acid/acetate, citric acid/citrate, glutamic acid/glutamate, phosphoric acid/phosphate or any other suitable pH buffering system is obtained. Among them the most preferred pH buffering system is acetic acid/acetate which is suitably used in the concentrations of acetic acid at about 0.15 mM to about 15 mM, most preferably in the concentration range from 1.5 mM to 10 mM.

The pharmaceutical composition of the present invention may optionally further comprise a polyol which is selected from the group comprising: sorbitol, mannitol, inositol and glycerol. Among them, sorbitol is particularly preferred and is suitably used in the concentration at about 1% to about 10% (m/v), mostly preferred at concentrations from 3% to 8% (m/v).

The pharmaceutical composition of the present invention may optionally further comprise one of more pharmaceutically acceptable excipients. Suitable pharmaceutically acceptable excipients may be selected from the group comprising polyvinylpirolidone, polyethylenglycol, hydroxypropylcellulose-β-cyclodextrin, poloxamers, sugars such as sucrose and trehalose, hydroxypropylcellulose, methylcellulose, macrogol esters and ethers, glycol and glycerol esters and/or various amino acids The pharmaceutical composition of the present invention can be filled in ampoules, injection syringes, prefilled injection syringes, multi dose cartridges and vials. These enable the application in volumes in the suitable range which may be but is not limited to the range from 0.2 to 2 ml per dose.

Biologically active G-CSF stabilized in the pharmaceutical composition of the present invention can be used for treatment of the diseases selected from the group, which comprises: neutropenia and neutropenia-related clinical sequelae, reduction of hospitalisation for febrile neutropenia after chemotherapy, mobilisation of hematopoietic progenitor cells, as alternative to donor leukocyte infusion, chronic neutropenia, neutropenic and non-neutropenic infections, transplant recipients, chronic inflammatory conditions, sepsis and septic shock, reduction of rist, morbidity, mortality, number of days of hospitalisation in neutropenic and non-neutropenic infections, prevention of infection and infection-related complications in neutropenic and non-neutropenic patients, prevention of nosocomial infection and to reduce the mortality rate and the frequency rate of nosocomial infections, enteral administration in neonates, enhancing the immune system in neonates, improving the clinical outcome in intensive care unit patients and critically ill patients, wound/skin ulcers/burns healing and treatment, intensification of chemotherapy and/or radiotherapy, pancytopenia, increase of anti-inflammatory citokines, shortening of intervals of high-dose chemotherapy by the prophylactic employment of filgrastim, potentiation of the anti-tumor effects of photodynamic therapy, prevention and treatment of illness caused by different cerebral disfunctions, treatment of thrombotic illness and their complications and post irradiation recovery of erythropoiesis. It can be also used for treatment of all other illnesses, which are indicative for G-CSF.

The following examples illustrate the present invention without, however, limiting the same thereto.

EXAMPLES

Analytical Methods

The following analytical methods were used for the analysis of the pharmaceutical composition of the present invention: size exclusion HPLC (SE-HPLC), reverse phase HPLC (RP-HPLC), sodium dodecyl sulphate polyacrylamide gel electrophoresis (SDS-PAGE), melting point temperature (Tm) determination with UV detection, isoelectric focusing (IEF) and in vitro biological activity assay.

SE-HPLC

SE-HPLC was used to determine the concentration of aggregates of G-CSF, especially dimers and higher aggregates. Detection limit for dimers and higher aggregates is 0.01%.

High performance liquid chromatograph (HPLC) system was as follows: UV detector, online degasser, binary pump module and thermostated autosampler (e.g. Waters Alliance HPLC systems). The analyses were performed under the following conditions:

Chromatographic Conditions:
Column: TSK G3000 SW, 10 μm, 300×7.5 mm ID
Column temperature: 30° C.
Mobile phase: phosphate buffer pH 7.0 (5 mM sodium phosphate, 50 mM NaCl)
Flow rate: 0.8 ml/min, isocratic mode Detection: UV-Detector, Wavelength 215 nm.
Injection volume: 20 μl (injected amount of protein is 6-12 μg)
Autosampler temperature: +2 to +8° C.
Run time: 20 min

RP-HPLC

RP-HPLC was used to determine G-CSF content and to quantify impurities separated according to their hydrophobicity.

High performance liquid chromatograph system was used as follows: UV detector with online degasser, binary pump module, thermostated autosampler and thermostated column department (e.g. Waters Alliance HPLC systems). The analyses were performed under the following conditions:

Chromatographic Conditions:
Column: YMC-Pack ODS-AQ, 200 Å, spherical, 3 μm, 150×4.6 mm i.d.
Column temperature: 65° C.
Mobile phase: Phase A: 0.1% trifluoro acetic acid (TFA) and 50% acetonitrile (ACN) in water
Phase B: 0.1% TFA and 95% ACN in water for HPLC
Flow rate: 1.0 mL/min, gradient mode according to scheme:

| Time [min] | Mobile phase B [%] |
|---|---|
| 0.0 | 8 |
| 4.0 | 8 |
| 19.0 | 28 |
| 19.1 | 100 |
| 21.0 | 100 |
| 21.1 | 8 |
| 25.0 | 8 |

Detection: UV-Detector, Wavelength 215 nm.
Injection volume: 10 μL (injected amount of protein is 3-6 μg)
Autosampler temperature: +2 to +8° C.
Run time: 25 min Tm Determination with UV Detection Tm was used for the estimation of protein conformation stability. High Tm indicates higher protein stability in certain composition. G-CSF stability is generally improved by the addition of certain excipients.

UV spectrophotometer with Peltier cooling heating system (DBS, PTP-1): Perkin Elmer Lambda BIO 40 spectrophotometer was used. The analyses were performed under the following conditions:

Temperature range: 50-70° C.
Temperature rate: 1° C./min
Detection: Wavelength 280 nm.
Sample volume: 1.0 ml (concentration of protein: 0.3-0.6 mg/ml)
Autosampler temperature: +2 to +8° C.

SDS-PAGE

SDS-PAGE was used to detect visually the appearance of protein dimers and other aggregated forms (trimers and higher molecular mass forms).

The loading samples were prepared in the loading buffer free of reducing agent. The vertical SDS-PAGE was used: gel NuPAGE Bis-TRIS 12%, 8×8 cm, thickness 1.0 mm, 15 lanes (Invitrogen) in MOPS SDS electrophoresis buffer (Invitrogen). Electrophoresis ran at constant voltage of 200 V. The samples were analysed by staining with Commassie blue (0.1% Phast Gel Blue R 350 in 30% methanol).

In vitro G-CSF Biological Activity Assay

Biological activity of G-CSF was determined by the method based on stimulation of cellular proliferation (NFS-60 cells) using the known method (Hammerling U et al (1995) *J Pharm Biomed Anal* 13:9-20) and the use of international standard Human recombinant G-CSF (88/502, yeast cell derived; NIBSC Potters Bar, Hertfordshire, UK); (Mire-Sluis A R et al (1995) *J Immunol Methods* 179, 117-126).

pH Value Measurement pH values were determined by using MA 5741 (Iskra) pH meter and Biotrode (Hamilton) electrode. The pH meter was calibrated to the pH value range from pH 3.0 to pH 5.0 with suitable fresh calibration buffers. pH was measured 25° C. The standard deviation of the pH measurements is 0.003 of a pH value (0.3%).

Conditions for Testing the G-CSF Stability in the Pharmaceutical Compositions

4° C.: stored in the refrigerator at the refrigerator temperature (ranging from +4° C. to +6° C.)

40° C.: stored at 40° C.±2° C.

25° C.: stored at room temperature ranging form 25° C. to 30° C. in 1 ml prefilled syringes by shaking in at 75 RPM on Vibromix 314EVT shaker.

Example 1

Stability Tests

The following pharmaceutical compositions of G-CSF were prepared:

S18: 1.5 mg/ml G-CSF, pH adjusted with acetic acid to 4.4

B1a (0.3): 0.3 mg/ml G-CSF, 1.5 mM acetic acid, 5% (w/v) sorbitol, pH adjusted to 4.2 with diluted solution of NaOH B1b (0.3): 0.3 mg/ml G-CSF, 1.5 mM acetic acid, 5% (w/v) sorbitol, pH adjusted to 4.4 with diluted solution of NaOH B1c (0.3): 0.3 mg/ml G-CSF, 1.5 mM acetic acid, 5% (w/v) sorbitol, pH adjusted to 4.6 with diluted solution of NaOH B1d (0.3): 0.3 mg/ml G-CSF, 1.5 mM acetic acid, 5% (w/v) sorbitol, pH adjusted to 4.8 with diluted solution of NaOH B1e (0.3): 0.3 mg/ml G-CSF, 0.13 mM acetic acid, 5% (w/v) sorbitol, pH 4.4

B-1e-3 (0.3): 0.3 mg/ml G-CSF, 0.13 mM citric acid, 5% (w/v) sorbitol, pH 4.4

B-1e-4 (0.3): 0.3 mg/ml G-CSF, 0.13 mM maleic acid, 5% (w/v) sorbitol, pH 4.4

B1f (0.3): 0.3 mg/ml G-CSF, 1.5 mM acetic acid, 5% (w/v) sorbitol, pH adjusted to 4.4 with TRIS B-1b (0.6): 0.6 mg/ml G-CSF, 1.5 mM acetic acid, 8% (w/v) sorbitol, pH adjusted to 4.4 with diluted solution of NaOH B-1e (0.6): 0.6 mg/ml G-CSF, 0.13 mM acetic acid, 8% (w/v) sorbitol, pH 4.4

B-1e-2 (0.6): 0.6 mg/ml G-CSF, 1.5 mM acetic acid, 8% (w/v) sorbitol, 0.004% Tween 80, pH adjusted to 4.4 with diluted solution of NaOH B-1e-3 (0.6): 0.6 mg/ml G-CSF, 0.13 mM citric acid, 8% (w/v) sorbitol, pH 4.4

B-1e-4 (0.6): 0.6 mg/ml G-CSF, 0.13 mM maleic acid, 8% (w/v) sorbitol, pH 4.4

B-1g (0.6): 0.6 mg/ml G-CSF, 0.04 mM HCl, 8% (w/v) sorbitol, pH 4.4

B2a (0.3): 0.3 mg ml G-CSF, 1.5 mM acetic acid, 3% (w/v) sorbitol, pH adjusted to 4.2 with diluted solution of NaOH B2b (0.3): 0.3 mg/ml G-CSF, 1.5 mM acetic acid, 3% (w/v) sorbitol, pH adjusted to 4.4 with diluted solution of NaOH B-3b (0.3): 0.3 mg/ml G-CSF, 0.04 mM methansulphonic acid, 5% (w/v) sorbitol, pH 4.4

B-4a (0.3): 0.3 mg/ml G-CSF, 1.5 mM acetic acid, 5% (w/v) glycerol, pH 4.4

B-4c (0.3): 0.3 mg/ml G-CSF, 1.5 mM acetic acid, 5% (w/v) glycerol, 0.1% Poloxamer 188, pH 4.4

B-5a (0.6): 0.6 mg/ml G-CSF, 1.5 mM acetic acid, 8% (w/v) sorbitol, 0.1% Tween 20, pH adjusted to 4.4 with diluted solution of NaOH B-6a (0.3): 0.3 mg/ml G-CSF, 1.5 mM acetic acid, 5% (w/v) sorbitol, 0.05% Poloxamer 188, pH 4.4

B-6b (0.3): 0.3 mg/ml G-CSF, 1.5 mM acetic acid, 5% (w/v) sorbitol, 0.1% Poloxamer 188, pH 4.4

B-6d (0.3): 0.3 mg/ml G-CSF, 1.5 mM acetic acid, 5% (w/v) sorbitol, 1.0% Poloxamer 188, pH 4.4

D2a (0.3): 0.3 mg/ml G-CSF, 0.04 mM methansulphonic acid, 5% (w/v) sorbitol, 0.1% Poloxamer 188, pH 4.4

D2b (0.3): 0.3 mg/ml G-CSF, 10 mM methansulphonic acid, 5% (w/v) sorbitol, 0.1% Poloxamer 188, pH adjusted to 4.4 with diluted solution of NaOH S12: 1.0 mg/ml G-CSF, 10 mM acetic acid, 5% (m/v) sorbitol, pH adjusted to 4.0 with NaOH Reference Compositions A (S16-10ACT): 0.3 mg/ml G-CSF, 10 mM acetic acid, 5% (m/v) sorbitol, 0.004% Tween 80, pH adjusted to 4.0 with NaOH (Neupogen like)

B (S16-10ACT): 0.3 mg/ml G-CSF, 1.5 mM acetic acid, 5% (m/v) sorbitol, 0.004% Tween 80, pH adjusted to 3.8 with HCl N: Neupogen composition available in the market (G-CSF concentration of 0.6 mg/ml)

Sample S18 with a respective G-CSF content of 1.5 mg/ml was stored at 4° C. for 3 months. The sample was analyzed by SE-HPLC; 12 μg of G-CSF were loaded into the column. FIG. 1 shows the results (AU=absorption unit).

Figure 2:
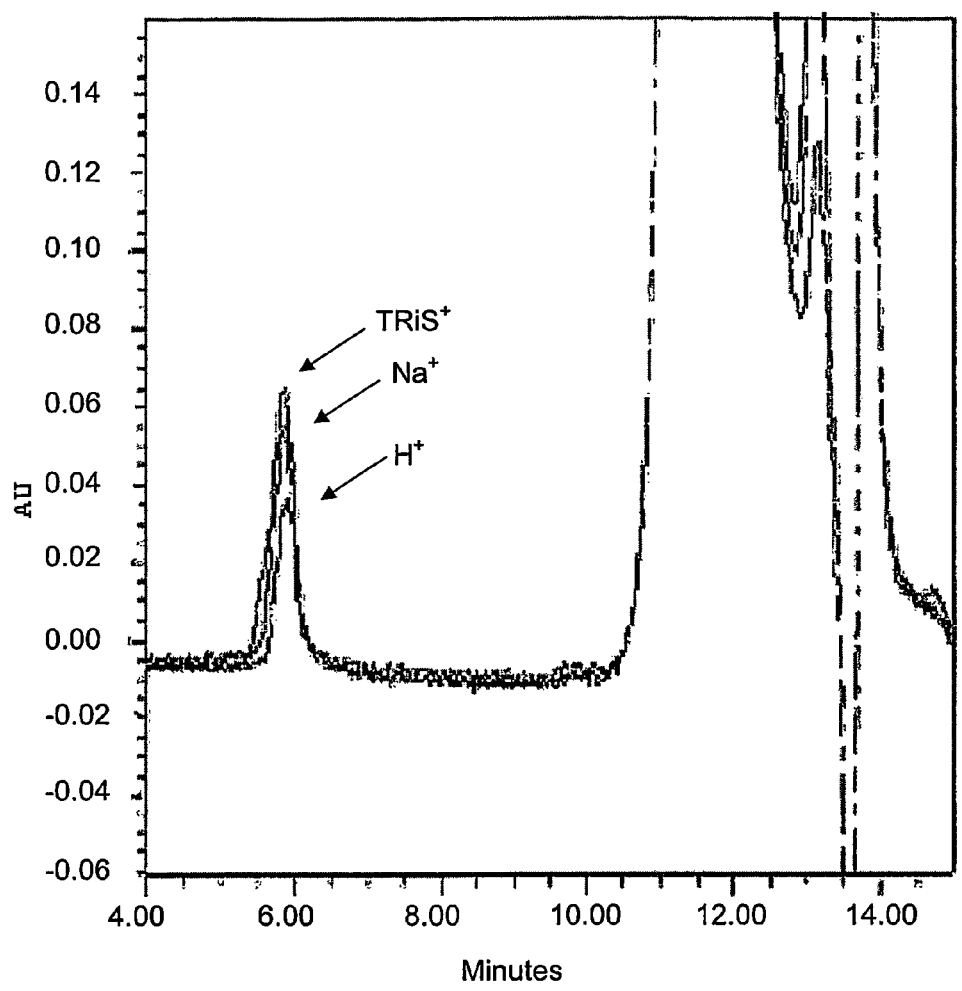
FIG. 2 shows SE-HPLC analysis of inventive and reference samples comprising G-CSF after having been stored at 40° C. for 1 month.

Samples with a respective G-CSF content of 0.3 mg/ml were stored at 40° C. for 1 month. The samples were analyzed by SE-HPLC; 6 μg of G-CSF were loaded into the column. FIG. 2 shows the selected results (AU=absorption unit).

Legend of FIG. 2:

$H^+$ B-1e (0.3)

$Na^+$ B-1b (0.3)

$TRIS^+$ B-1f (0.3)

Figure 3:
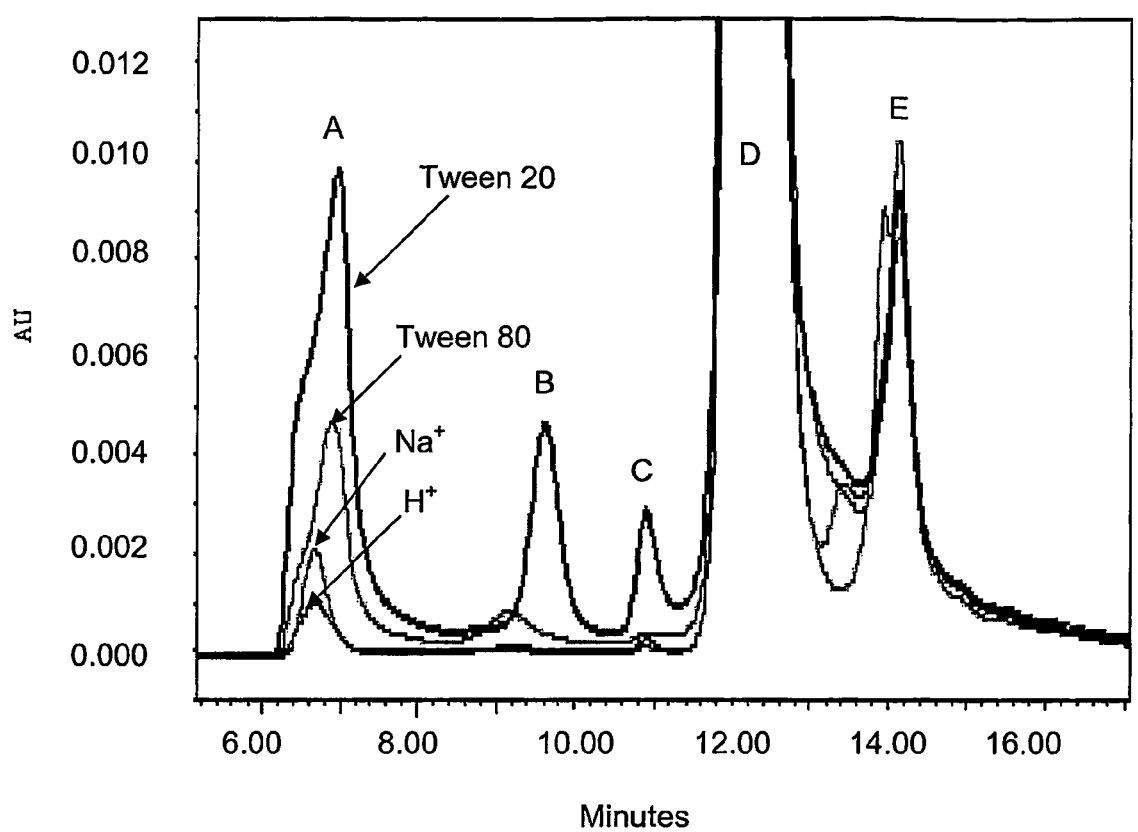
FIG. 3 shows SE-HPLC analysis of inventive and reference samples comprising G-CSF after having been stored at 40° C. for 1 month.

FIG. 3 shows the SE-HPLC of some samples with a respective G-CSF content of 0.6 mg/ml stored at 40° C. for 1 month. 12 μg of G-CSF were loaded into the column. (AU=absorption unit)

Legend of FIG. 3:

$H^+$ higher aggregates of B-1e (0.6)

$Na^+$ higher aggregates of B-1b (0.6)

Tween 80 higher aggregates of B-1e-2 (0.6)

Tween 20 higher aggregates of B-5a (0.6)

A higher aggregates

B response of placebo comprising Tween 20

C dimers

D G-CSF monomer

E response of placebo comprising Tween 20

Figure 4:
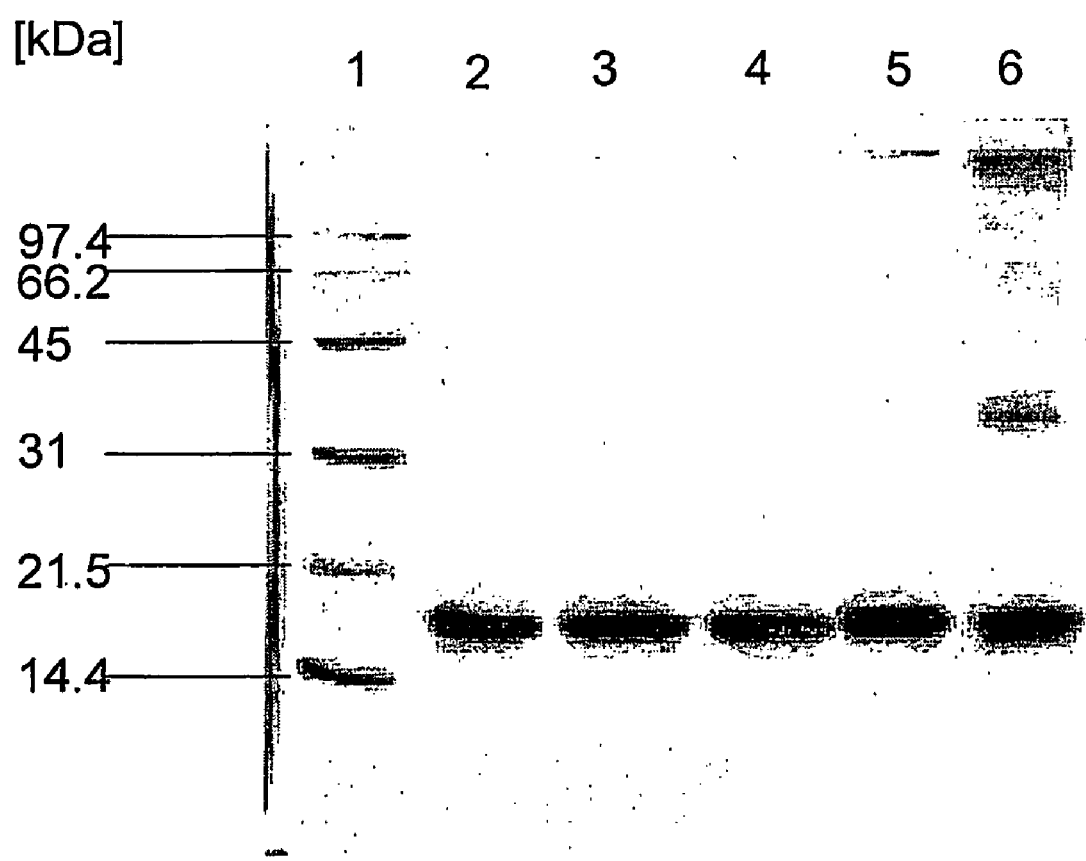
FIG. 4 shows SDS-PAGE analysis of inventive and reference samples comprising G-CSF after having been stored at 40° C. for 1 month.

FIG. 4 shows SDS-PAGE analysis of the inventive and reference samples with a respective G-CSF content of 0.6 mg/ml stored at 40° C. for 1 month. N (0.3 mg/ml) used as reference control was stored at the same conditions. 1 μl was loaded in each lane.

Legend of FIG. 4:

Lane 1: Low molecular weight protein standards (0.79 μg)

Lane 2: N (1 μg)

Lane 3: B-1e (0.6)

Lane 4: B-1b (0.6)

Lane 5: B-1e-2 (0.6)

Lane 6: B-5a (0.6)

Figure 5:
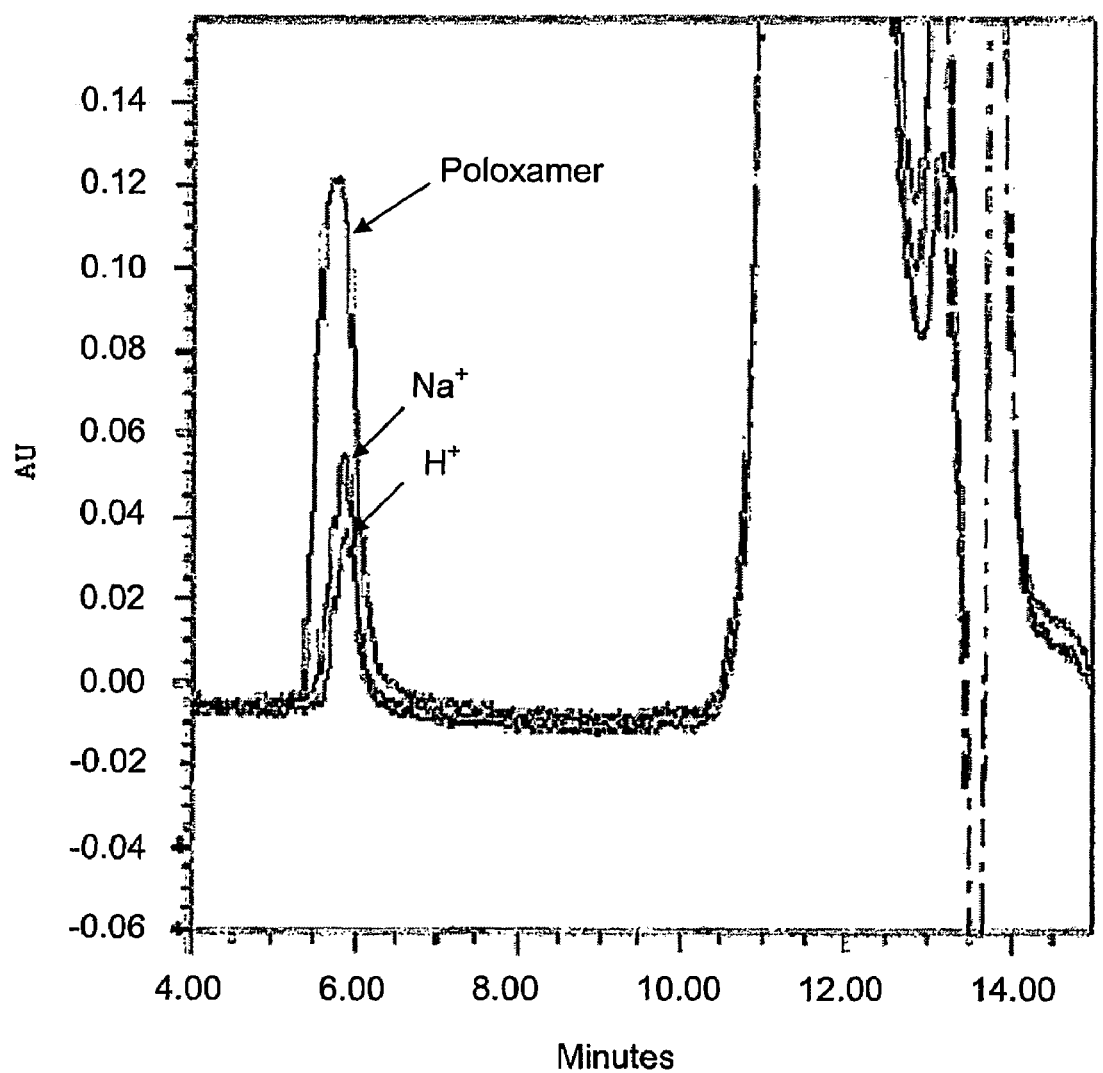
FIG. 5 shows SE-HPLC analysis of inventive and reference samples comprising G-CSF after having been stored at 40° C. for 1 month.

FIG. 5 shows the SE-HPLC of some samples with a respective G-CSF content of 0.3 mg/ml stored at 40° C. (±2° C.) 1 month (40). 12 μg was loaded into the column.

Legend of FIG. 5:

$H^+$ higher aggregates of B-1e (0.3)

$Na^+$ higher aggregates of B-1b (0.3)

Poloxamer higher aggregates of B-6b (0.3)

Results of Stability Tests:

SE-HPLC analyses of the sample S18 stored for 2 and 3 months at 4° C. show that the dimers and higher aggregates are either not detected or are detected in small amounts (Table 1, FIG. 1).

These results a re comparable to the G-CSF stability in the composition of G-CSF (AS16-10ACT) which is identical to the G-CSF composition available in the market (Neupogen (G-CSF=0.3 mg/ml), non-glycosylated G-CSF) (Table 1).

Tm of the sample S18 is comparable to Tm of AS16-10ACT indicating that the G-CSF stability in S18 can be expected to be comparable to the G-CSF stability in AS16-10ACT. This is confirmed by the stability study at +4° C. (Table 1).

Furthermore, the G-CSF stability was confirmed also by SDS-PAGE analysis (results not shown). In addition, RP-HPLC analysis did not show significant changes in impurities or protein content after storage time (results not shown). The in vitro biological activity of G-CSF used for the inventive composition was at the level of international standard (Cat. No. 88/502; NIBSC, UK). After several months storage the biological activity of G-CSF stored in the composition S18 was not changed.

TABLE 1

|  | pH | Storage time | Temperature | Dimers (SE-HPLC) | Higher aggregates (SE-HPLC) | Tm (° C.) |
|---|---|---|---|---|---|---|
| AS16-10ACT | 4.0 | 1 m | 40° C. | 0.00% | 0.13% | 66.9 |
| c = 0.3 mg/ml |  | 1 m | 4° C. | 0.00% | 0.00% |  |
| S18 | 4.4 | 2 m | 4° C. | 0.02% | 0.00% | *67.2 |
| c = 1.5 mg/ml |  | 3 m | 4° C. | 0.02% | 0.00% |  | m: month;
%: amount of dimers/higher aggregates to the total amount of G-CSF, c = G-CSF concentration,
*Tm measured at G-CSF concentration = 0.3 mg/ml These results show that after several months storage at proper conditions (initial part of long term stability study) the complete G-CSF stability in the sample S18 is achieved. The G-CSF stability in S18 is better or comparable to the sample AS16-10ACT although in S18 no additional G-CSF stabilizers (e.g. surfactants) are added, the concentration of G-CSF is five fold higher, the storage time is longer and the pH value is well above 4.0 (4.4).

The influence of different buffer systems was tested in a series of compositions with 1.5 mM acetic acid adjusted to pH value of 4.4 with different bases (NaOH, TRIS) and in a composition with pH value of 4.4 achieved with acetic acid only. The results of the analyses are presented in Table 2 and in FIG. 2.

TABLE 2

|  | Counter ion | Storage time | Temperature | Dimers (SE-HPLC) | Higher aggregates (SE-HPLC) | Tm (° C.) |
|---|---|---|---|---|---|---|
| B-1f (0.3) | $TRIS^+$ | 1 w | 40° C. | 0.01% | 0.02% | 61.3 |
|  |  | 1 m | 40° C. | 0.00% | 0.65% |  |
| B-1b (0.3) | $Na^+$ | 1 w | 40° C. | 0.00% | 0.01% | 60.3 |
|  |  | 1 m | 40° C. | 0.00% | 0.46% |  |
| B-1e (0.3) | $H^+$ | 1 w | 40° C. | 0.01% | 0.04% | 66.5 |
|  |  | 1 m | 40° C. | 0.00% | 0.31% |  | m: month;
w: week;
%: amount of dimers/higher aggregates to the total amount of G-CSF The results show a difference in Tm and in the content of higher aggregates when various cations are used. Tm of the composition comprising pure acid is higher in comparison to the composition comprising $Na^+$ and $TRIS^+$ cations. Consistently, the content of aggregates is the lowest in the composition comprising pure acid comparing to the compositions which comprised $Na^+$ and $TRIS^+$ cations. In addition, RP-HPLC analyses do not show significant changes in content and profile of impurities after the storage time (results not shown). These results indicate that pure acid ($H^+$) is preferential for G-CSF stability in comparison to $TRIS^+$ and $Na^+$.

The influence of pH on G-CSF stability was tested in a series of compositions comprising 1.5 mM acetic acid/acetate buffering system at pH values of 4.2, 4.4, 4.6 and 4.8. The results of SE-HPLC analyses are presented in Table 3.

TABLE 3

|  | pH | Storage time | Temperature | Dimers (SE-HPLC) | Higher aggregates (SE-HPLC) |
|---|---|---|---|---|---|
| B-1a (0.3) | 4.2 | 1 w | 40° C. | 0.00% | 0.00% |
|  |  | 1 m | 40° C. | 0.00% | 0.20% |
| B-1b (0.3) | 4.4 | 1 w | 40° C. | 0.00% | 0.01% |
|  |  | 1 m | 40° C. | 0.00% | 0.46% |
| B-1c (0.3) | 4.6 | 1 w | 40° C. | 0.00% | 0.01% |
| B-1d (0.3) | 4.8 | 1 w | 40° C. | 0.00% | 0.02% | m: month;
w: week,
%: amount of dimers/higher aggregates to the total amount of G-CSF In the pH range from 4.2 to 4.8 no essential differences in dimers occurrence is detected at 40° C.

The influence of polysorbates (surfactant) on the G-CSF stability was tested with compositions comprising 0.6 mg/ml G-CSF. The results are presented in Table 4 and in FIGS. 3 and 4.

TABLE 4

|  | Surfactant | Storage time | Temperature | Dimers (SE-HPLC) | Higher aggregates (SE-HPLC) | Protein content (RP-HPLC) | Tm (° C.) |
|---|---|---|---|---|---|---|---|
| B-1b (0.6) | — | 1 w | 40° C. | 0.00% | 0.00% |  | 63.4 |
|  |  | 1 m | 40° C. | 0.03% | 0.06% | 94.8% |  |

TABLE 4-continued

| | Surfactant | Storage time | Temperature | Dimers (SE-HPLC) | Higher aggregates (SE-HPLC) | Protein content (RP-HPLC) | Tm (° C.) |
|---|---|---|---|---|---|---|---|
| | | 1 w shaking | 25° C. | 0.08% | 0.04% | | |
| B-1e (0.6) | — | 1 w | 40° C. | 0.00% | 0.00% | | 64.4 |
| | | 1 m | 40° C. | 0.03% | 0.08% | 94.1% | |
| | | 1 w shaking | 25° C. | 0.04% | 0.08% | | |
| B-1g (0.6) | — | 1 w | 40° C. | 0.00% | 0.00% | | 64.6 |
| | | 1 m | 40° C. | 0.03% | 0.10% | 93.8% | |
| | | 1 w shaking | 25° C. | 0.02% | 0.03% | | |
| B-1e-2 (0.6) | 0.004% Tween 80 | 1 w | 40° C. | 0.00% | 0.00% | | 63.6 |
| | | 1 m | 40° C. | 0.02% | 0.16% | 91.8% | |
| | | 1 w shaking | 25° C. | 0.02% | 0.05% | | |
| B-5a (0.6) | 0.1% Tween 20 | 1 w | 40° C. | 0.00% | 0.00% | | 62.5 |
| | | 1 m | 40° C. | 0.12% | 0.62% | 42.7% | |
| | | 1 w shaking | 25° C. | 0.65 | 0.32 | | | m: month;
w: week;
%: amount of dimers/higher aggregates to the total amount of G-CSF The results presented in Table 4 reveal that by the addition of surfactant polysorbate 20 (Tween 20) or polysorbate 80 (Tween 80) the G-CSF stability is not improved. The results show that the G-CSF stability is achieved without the addition of surfactant. Additionally, RP-HPLC analyses of protein content reveal that in compositions comprising the polysorbates the protein content is lower.

The influence of poloxamer (block copolymer) on the G-CSF stability was tested with compositions comprising 0.3 mg/ml G-CSF. The results are presented in Tables 5 and 6 and in FIG. 5.

TABLE 5

| | Block copolymer | Tm (° C.) |
|---|---|---|
| B-6a (0.3) | 0.05% Poloxamer 188 | 61.3 |
| B-6b (0.3) | 0.10% Poloxamer 188 | 61.1 |
| B-6d (0.3) | 1.00% Poloxamer 188 | 56.7 | m: month;
w: week,
% Poloxamer: w/v

The results in Table 5 show that Tm is decreased with the addition of poloxamer 188.

TABLE 6

| | Block polymer | Storage time | Temperature | Dimers (SE-HPLC) | Higher aggregates (SE-HPLC) |
|---|---|---|---|---|---|
| B1b (0.3) | — | 1 m | 40° C. | 0.00% | 0.46% |
| B-6b (0.3) | 0.10% Poloxamer 188 | 1 m | 40° C. | 0.00% | 1.6% |
| B-4a (0.3) | — | 1 m | 40° C. | 0.00% | 0.50% |
| B-4c (0.3) | 0.10% Poloxamer 188 | 1 m | 40° C. | 0.00% | 1.02% | m: month;
w: week;
%: amount of dimers/higher aggregates to the total amount of G-CSF,
% Poloxamer: w/v:

The results presented in Table 6 reveal that by the addition of block copolymer poloxamer 188 the G-CSF stability is not improved.

The results presented in Tables 4, 5 and 6 indicate that polysorbates and poloxamers are not appropriate excipients for maintaining the G-CSF stability in G-CSF pharmaceutical compositions.

The influence of different acids on G-CSF stability was tested in a series of compositions comprising acetic acid, maleic acid, citric acid and methansulfonic acid. The results are presented in Table 7.

TABLE 7

| | Acid | Storage time | Temperature | Dimers (SE-HPLC) | Higher aggregates (SE-HPLC) | Tm (° C.) |
|---|---|---|---|---|---|---|
| B-1e (0.6) | acetic acid | 1 w | 40° C. | 0.00% | 0.00% | 64.4 |
| | | 1 m | 40° C. | 0.03% | 0.08% | |
| B-1e-3 (0.6) | citric acid | 1 w | 40° C. | 0.00% | 0.00% | 64.2 |
| | | 1 m | 40° C. | 0.03% | 0.08% | |
| | maleic acid | 1 w | 40° C. | 0.00% | 0.00% | 64.2 |
| B-1e-4 (0.6) | maleic acid | 1 w | 40° C. | 0.00% | 0.00% | 64.2 |
| | | 1 m | 40° C. | 0.03% | 0.07% | |
| B-3b (0.3) | methan-sulphonic acid | 1 w | 40° C. | 0.00% | 0.09% | 64.1 |
| | | 1 m | 40° C. | 0.00% | 0.22% | | m: month;
w: week;
%: amount of dimers/higher aggregates to the total amount of G-CSF The results of compositions with different acids used are comparable, with the acetic acid showing slightly better G-CSF stability.

The influence of polyol selection and its concentration to the G-CSF stability was tested in a series of compositions comprising sorbitol and glycerol. The results are presented in Table 8.

TABLE 8

| | Polyol | Storage time | Temperature | Dimers (SE-HPLC) | Higher aggregates (SE-HPLC) | Tm (° C.) |
|---|---|---|---|---|---|---|
| B-1b (0.3) | 5% sorbitol. pH 4.4 | 1 w<br>1 m | 40° C.<br>40° C. | 0.00%<br>0.00% | 0.01%<br>0.46% | 60.3 |
| B-2b (0.3) | 3% sorbitol, pH 4.4 | 1 w<br>1 m | 40° C.<br>40° C. | 0.00%<br>0.00% | 0.01%<br>0.65% | 61.9 |
| B-4a (0.3) | 5% glycerol, pH 4.4 | 1 w<br>1 m | 40° C.<br>40° C. | 0.00%<br>0.00% | 0.00%<br>0.50% | 61.4 | m: month;
w: week;
%: amount of dimers/higher aggregates to the total amount of G-CSF,
% polyol: (w/v)

The results in Table 8 reveal that either sorbitol or glycerol can be used for efficient G-CSF stability. The results of RP-HPLC analyses do not differ significantly between the compositions presented in Table 8 (results not shown).

Example 2

Compositions of the Inventive Pharmaceutical Compositions of G-CSF

The compositions of inventive pharmaceutical compositions are set out in Table 9.

TABLE 9

| Sample | G-CSF content (mg/ml) | Inactive ingredients | pH |
|---|---|---|---|
| S18 | 1.5 | acetic acid (for pH adjustment) | 4.4 |
| B1e (0.3): | 0.3 | 0.13 mM acetic acid, 5% (w/v) sorbitol | 4.4 |
| B-1g (0.6) | 0.6 | 0.04 mM HCl, 8% (w/v) sorbitol, | 4.4 |
| B-1e-4 (0.3) | 0.3 | 0.13 mM maleic acid, 5% (w/v) sorbitol | 4.4 |
| B-1e (0.6) | 0.6 | 0.13 mM acetic acid, 8% (w/v) sorbitol | 4.4 |
| B-1g (0.6) | 0.6 | 0.04 mM HCl, 8% (w/v) sorbitol | 4.4 |
| B-1e-3 (0.6) | 0.6 | 0.13 mM citric acid, 8% (w/v) sorbitol | 4.4 |
| B-1e-4 (0.6) | 0.6 | 0.13 mM maleic acid, 8% (w/v) sorbitol | 4.4 |
| B-1e-3 (0.3) | 0.3 | 0.13 mM citric acid, 5% (w/v) sorbitol | 4.4 |
| B2a (0.3) | 0.3 | 1.5 mM acetic acid, 3% (w/v) sorbitol, NaOH (for pH adjustment) | 4.2 |
| B2b (0.3) | 0.3 | 1.5 mM acetic acid, 3% (w/v) sorbitol, NaOH (for pH adjustment) | 4.4 |
| B1a (0.3) | 0.3 | 1.5 mM acetic acid, 5% (w/v) sorbitol, NaOH (for pH adjustment) | 4.2 |
| B1b (0.3) | 0.3 | 1.5 mM acetic acid, 5% (w/v) sorbitol, NaOH (for pH adjustment) | 4.4 |
| B1c (0.3) | 0.3 | 1.5 mM acetic acid, 5% (w/v) sorbitol, NaOH (for pH adjustment) | 4.6 |
| B1d (0.3) | 0.3 | 1.5 mM acetic acid, 5% (w/v) sorbitol, NaOH (for pH adjustment) | 4.8 |
| B-1b (0.6) | 0.6 | 1.5 mM acetic acid, 8% (w/v) sorbitol, NaOH (for pH adjustment) | 4.4 |
| B-3b (0.3) | 0.3 | 0.04 mM methansulphonic acid, 5% (w/v) sorbitol | 4.4 |
| B-4a (0.3) | 0.3 | 1.5 mM acetic acid, 5% (w/v) glycerol | 4.4 |

Preparation of Bulk Concentrate:

The starting material of G-CSF which was used for the preparation the bulk concentrate of G-CSF was produced by the expression in *E. coli* (non-glycosylated G-CSF).

Bulk concentrate of G-CSF was prepared in solution of pure acid (acetic acid or HCl) pH value of 4.4 at G-CSF concentration of 1.5 mg/ml. The SE-HPLC analysis of the bulk concentrate showed that the content of dimers and higher aggregates was below the detection limit. The content of impurities observed in RP-HPLC analysis was in the range of 2-4%. (The analyses of fresh Neupogen samples showed comparable or higher level of impurities observed in RP-HPLC analyses.)

Quality of Excipients:

Acetic acid: Ph Eur quality; HCl: Merck 32% for analysis; maleic acid: USP quality; citric acid: Merck, for analysis; methansulphonic acid; Fluka; NaOH: Ph Eur quality; sorbitol: Ph Eur quality; glycerol: Merck; for analysis; Poloxamer 188: BASF, Pluronic F68, NF grade; Tween 20: Sigma, low-peroxide, low-carbonyls, contains BHT as antioxidant; Tween 80 (Sigma, low peroxide, contains BHT as antioxidant); water for injection: Ph Eur quality; water for analyses (water): Milli-Q (Millipore)

Preparation of Reference Pharmaceutical Compositions:

A (S16-10ACT): Bulk concentrate of G-CSF (1.5 mg/ml) was diluted five fold with buffer containing 12.5 mM acetic acid adjusted to pH 4.0 with diluted solution of NaOH, 6.25% sorbitol and 0.005% (w/v) Tween 80. The pH value of the final composition was 4.0±0.1.

A (S16-1.5ACT): Bulk concentrate of G-CSF was diluted five fold with buffer containing 1.875 mM acetic acid adjusted to pH 4.0 with diluted solution of NaOH, 6.25% (w/v) sorbitol and 0.005% (w/v) Tween 80. The pH of the final composition was 4.0±0.1.

Preparation of the Inventive Pharmaceutical Compositions:

Generally:

The inventive pharmaceutical compositions were prepared by dilution of the sterile bulk concentrate of G-CSF with appropriate sterile buffer solutions which were previously filtered through 0.2 PES/Nalgene filter. The final concentrations of G-CSF were 0.3 mg/ml or 0.6 mg/ml, respectively.

The filtered solutions were filled in 2 ml vials (vials from the colorless tubular glass hydrolytic type I) washed and sterilized, and closed with elastic closures from brombutyl rubber and, sealed with aluminium caps.

S18: After last purification step protein solution was ultrafiltrated against water acidified with acetic acid (pH 4.4). Labscale TFF System/Millipore with three Pellicon XL Ultracell-5PLCCC/Millipore filters was used. Ultrafiltration of G-CSF solution was performed against ten volumes of acidified water previously filtered through 0.2 PES/Nalgene. The conductivity and pH were measured. The final G-CSF concentration was 1.5 mg/ml. Sterile filtration of the protein solution through sterile 0.22 μm PVDF filters was performed after that.

B-1e (0.3): Bulk concentrate of G-CSF was diluted five fold with the solution containing 0.16 mM acetic acid, 6.25% (w/v) sorbitol. In the compositions B-1e-4 (0.3), B-1e-3 (0.3), B-3b (0.3) the appropriate amount of other acid e.g. citric acid, maleic acid methansulphonic acid was used to achieve pH 4.4 in similar compositions. The pH of final composition was 4.4±0.1.

B-1a (0.3), B-1b (0.3), B-1c (0.3), B-1d (0.3): Bulk concentrate of G-CSF was diluted five fold with buffer containing 1.875 mM acetic acid adjusted to pH 4.2 (4.4, 4.6, 4.8) with diluted solution of NaOH and 6.25% (w/v) sorbitol. The pH of final composition was 4.2±0.1 (4.4±0.1; 4.6±0.1; 4.8±0.1, respectively).

B-1b (0.6): Bulk concentrate of G-CSF (1.5 mg/ml) was diluted two and half fold with the 2.5 mM acetic acid adjusted to pH 4.4 with diluted solution of NaOH and 13.3% (w/v) sorbitol. The pH of the final composition was 4.4±0.1.

B-1e (0.6), B-1e-3 (0.6), B-1e-4 (0.6), B-1g (0.6): Bulk concentrate of G-CSF (1.5 mg/ml) was diluted two and half fold with the solution containing 0.22 mM acetic acid, 13.3% (w/v) sorbitol. In other cases appropriate amount of other acid e.g. citric acid or maleic acid was used to achieve pH 4.4 in the similar compositions. The pH of the final composition was 4.4±0.1.

B-2a (0.3), B-2b (0.3): Bulk concentrate of G-CSF was diluted five fold with buffer containing 1.875 mM acetic acid adjusted to pH 4.2 or 4.4 with diluted solution of NaOH and 3.75% (w/v) sorbitol. The pH of final composition was 4.2±0.1 or 4.4±0.1; respectively.

B-4a (0.3): Bulk concentrate of G-CSF was diluted five fold with the buffer containing 1.875 mM acetic acid adjusted to pH 4.4 with diluted solution of NaOH and 6.25%. (w/v) glycerol. The pH of the final composition was 4.4±0.1.

The invention claimed is:

1. A stable pharmaceutical composition of granulocyte-colony stimulating factor (G-CSF) comprising:
   a therapeutically effective amount of a non-glycosylated G-CSF in a concentration ranging from about 0.3 mg/ml to about 0.96 mg/ml, and
   an acid, wherein the composition is free of any surfactant, the composition is an aqueous liquid, and the composition has a pH value ranging from about 4.2 to about 4.8
   wherein the amount of G-CSF higher aggregates in the composition after storage for 1 month at 40 degrees C. is no more than about 0.65% of the amount of G-CSF in the composition.

2. The composition of claim 1, wherein the pH of the composition is at about 4.4.

3. The composition according to claim 1 further comprising:
   a. a pH buffering system and/or
   b. one or more pharmaceutically acceptable excipient(s).

4. The composition of claim 1, wherein the acid is selected from the group consisting of acetic acid, HCl, maleic acid, glutamic acid, methansulphonic acid, citric acid, malonic acid, lactic acid, sulphuric acid, and phosphoric acid.

5. The composition of claim 4, wherein the acid is selected from the group consisting of acetic acid and HCl.

6. The composition of claim 1 further comprising a polyol is selected from the group consisting of sorbitol, glycerol, inositol and mannitol.

7. The composition of claim 6, wherein the polyol is sorbitol.

8. The composition of claim 7, wherein sorbitol is present in an amount from about 1% to about 10%.

9. The composition of claim 7, wherein sorbitol is present in an amount from about 3% to about 8%.

10. The composition of claim 3 wherein the pH buffering system is selected from the group consisting of acetic acid/acetate and phosphoric acid/phosphate.

11. The composition of claim 10, wherein the pH buffering system is acetic acid/acetate.

12. The composition of claim 11, wherein the concentration of acetic acid is in the range from about 0.15 mM to about 15 mM.

13. The composition of claim 12 wherein the concentration of acetic acid is in a range from about 1.5 mM to about 10 mM.

14. The composition of claim 1, wherein the pH of the composition is at about 4.2.

15. A stable pharmaceutical composition of granulocyte-colony stimulating factor (G-CSF) comprising:
   a therapeutically effective amount of a non-glycosylated G-CSF having a concentration ranging from about 0.3 mg/ml to about 0.96 mg/ml,
   a polyhydric alcohol selected from the group consisting of sorbitol, glycerol, inositol, mannitol, and mixtures thereof, and
   an acid, wherein the composition is free of a surfactant, the composition is an aqueous liquid, and the composition has a pH value ranging from about 4.2 to about 4.8
   wherein the amount of G-CSF higher aggregates in the composition after storage for 1 month at 40 degrees C. is no more than about 0.65% of the amount of G-CSF in the composition.

16. A stable pharmaceutical composition of granulocyte-colony stimulating factor (G-CSF) comprising a therapeutically effective amount of a non-glycosylated G-CSF and an acid, wherein the acid is the sole excipient, and wherein the composition has a pH value ranging from about 4.2 to about 4.8
   wherein the amount of G-CSF higher aggregates in the composition after storage for 1 month at 40 degrees C. is no more than about 0.65% of the amount of G-CSF in the composition.

17. The stable pharmaceutical composition of granulocyte-colony stimulating factor (G-CSF) of claim 1, wherein the amount of G-CSF higher aggregates in the composition after storage for 1 month at 40 degrees C. is no more than about 0.13% of the amount of G-CSF in the composition.

18. The stable pharmaceutical composition of granulocyte-colony stimulating factor (G-CSF) of claim 15, wherein the amount of G-CSF higher aggregates in the composition after storage for 1 month at 40 degrees C. is no more than about 0.13% of the amount of G-CSF in the composition.

19. The stable pharmaceutical composition of granulocyte-colony stimulating factor (G-CSF) of claim 16, wherein the amount of G-CSF higher aggregates in the composition after storage for 1 month at 40 degrees C. is no more than about 0.13% of the amount of G-CSF in the composition.

* * * * *

UNITED STATES PATENT AND TRADEMARK OFFICE
CERTIFICATE OF CORRECTION

PATENT NO. : 7,585,496 B2
APPLICATION NO. : 10/577285
DATED : September 8, 2009
INVENTOR(S) : Barbara Podobnik et al.

It is certified that error appears in the above-identified patent and that said Letters Patent is hereby corrected as shown below:

Column 3, lines 9-13, please delete the following sentences:

"The present invention provides a new stable pharmaceutical composition of G-CSF in accordance with claim 1. Preferred embodiments are set forth in the sub-claims. The present invention also provides a process according to claim 17, and uses according to claims 18 and 19."

In their place, please insert the following sentences:

--The present invention provides new stable pharmaceutical compositions of G-CSF in accordance with the disclosure herein. The specification also discloses preferred embodiments of the compositions and of processes and methods for making and using G-CSF compositions.--;

Column 3, line 34, "C." should be --C--;
Column 3, line 36, "C." should be --C--;
Column 3, line 39, "C." should be --C--;
Column 3, line 43, "C." should be --C--;
Column 3, line 45, "C." should be --C--;

Column 4, line 35, "highertemperature" should be --higher temperature--;
Column 4, line 48, "C." should be --C--;
Column 4, line 49, "C." should be --C--;
Column 4, line 50, "C." should be --C--;

Column 7, line 64, "C." should be --C--;
Column 8, line 4, "C." should be --C--;
Column 8, line 18, "C." should be --C--;
Column 8, line 39, "C." should be --C--;
Column 8, line 50, "C." should be --C--;
Column 8, line 51, "C." should be --C--;
Column 8, line 55, "C." should be --C--;

Column 9, line 18, "C." should be --C--;
Column 9, line 19, "C." should be --C--;
Column 9, line 20, "C." should be --C--;
Column 9, line 21, "C." should be --C--;
Column 9, line 22, "C." should be --C--;

CERTIFICATE OF CORRECTION (continued)
U.S. Pat. No. 7,585,496 B2

Column 10, line 28, "C." should be --C--;
Column 10, line 32, "C." should be --C--;
Column 10, line 42, "C." should be --C--;
Column 10, line 61, "C." should be --C--;

Column 11, line 7, "C." should be --C--;
Column 11, line 17, "C." should be --C--;
Column 11, line 20, "a re" should be --are--;
Column 11, Table 1, lines 42 through 46, "C." should be --C--;

Column 12, Table 2, lines 12 through 18, "C." should be --C--;
Column 12, Table 3, lines 43 through 48, "C." should be --C--;
Column 12, Table 4, lines 63 through 65, "C." should be --C--;

Column 13, Table 4 (continued), lines 4 through 23, "C." should be --C--;
Column 13, Table 5, line 42, "C." should be --C--;
Column 13, Table 6, lines 59-63, "C." should be --C--;
Column 14, Table 7, lines 44-55, "C." should be --C--;
Column 15, Table 8, line 6, "C." should be --C--;

Column 17, Claim 1, line 22, "C." should be --C--;
Column 18, Claim 15, line 21, "C." should be --C--;
Column 18, Claim 16, line 31, "C." should be --C--;
Column 18, Claim 17, line 37, "C." should be --C--;
Column 18, Claim 18, line 42, "C." should be --C--; and
Column 18, Claim 19, line 47, "C." should be --C--.

Signed and Sealed this

Fifth Day of January, 2010

David J. Kappos
*Director of the United States Patent and Trademark Office*